(12) United States Patent
Yoon et al.

(10) Patent No.: US 10,857,099 B2
(45) Date of Patent: *Dec. 8, 2020

(54) AMPHIPHILIC POLYMER

(71) Applicants: LG Chem, Ltd., Seoul (KR); LG Household & Health Care Ltd., Seoul (KR)

(72) Inventors: Jeong Ae Yoon, Daejeon (KR); Su Jeong Kim, Daejeon (KR); Sun Hwa Lee, Daejeon (KR); Woo Sun Shim, Daejeon (KR); Sung Soo Yoon, Daejeon (KR); Chang Hwan Ju, Daejeon (KR); Jung A. Kim, Daejeon (KR); Nae Gyu Kang, Daejeon (KR)

(73) Assignees: LG Chem, Ltd.; LG Household & Health Care Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 16/404,889

(22) Filed: May 7, 2019

(65) Prior Publication Data

US 2019/0254970 A1 Aug. 22, 2019

Related U.S. Application Data

(62) Division of application No. 15/525,835, filed as application No. PCT/KR2016/010623 on Sep. 23, 2016, now Pat. No. 10,328,024.

(30) Foreign Application Priority Data

Nov. 25, 2015 (KR) .......................... 10-2015-0165873

(51) Int. Cl.
*A61K 9/107* (2006.01)
*A61K 8/02* (2006.01)
(Continued)

(52) U.S. Cl.
CPC ............... *A61K 9/107* (2013.01); *A61K 8/02* (2013.01); *A61K 8/06* (2013.01); *A61K 8/11* (2013.01);
(Continued)

(58) Field of Classification Search
None
See application file for complete search history.

(56) References Cited

U.S. PATENT DOCUMENTS 10,143,651 B2 * 12/2018 Kim ..................... A61K 9/1075
10,251,819 B2 * 4/2019 Yoon ........................ A61K 9/51
(Continued)

FOREIGN PATENT DOCUMENTS

| CN | 101141877 A | 3/2008 |
| JP | 2009155282 A | 7/2009 |
| KR | 101549484 B1 | 9/2015 |

OTHER PUBLICATIONS

Search Report from International Application No. PCT/KR2016/010623, filed Dec. 23, 2016.
(Continued)

*Primary Examiner* — Aradhana Sasan
(74) *Attorney, Agent, or Firm* — Lerner, David, Littenberg, Krumholz & Mentlik, LLP (57) ABSTRACT

The present application relates to an amphiphilic polymer and a method of preparing the same. Furthermore, the present application relates to a micelle including a drug encapsulated by the amphiphilic polymer and a composition including the same. The amphiphilic polymer according to the present application has excellent drug encapsulation properties as well as good dispersion properties in an aqueous solution.

13 Claims, 1 Drawing Sheet

(51) Int. Cl.
| | |
|---|---|
| A61K 8/06 | (2006.01) |
| A61K 9/51 | (2006.01) |
| C08G 81/00 | (2006.01) |
| C08F 293/00 | (2006.01) |
| A61Q 19/00 | (2006.01) |
| A61K 8/90 | (2006.01) |
| A61K 8/11 | (2006.01) |
| A61K 9/00 | (2006.01) |
| A61K 31/352 | (2006.01) |
| C08G 81/02 | (2006.01) |

(52) U.S. Cl.
CPC .............. *A61K 8/90* (2013.01); *A61K 9/0014* (2013.01); *A61K 9/51* (2013.01); *A61K 9/5138* (2013.01); *A61K 31/352* (2013.01); *A61Q 19/00* (2013.01); *C08F 293/00* (2013.01); *C08G 81/00* (2013.01); *C08G 81/025* (2013.01); *A61K 2800/10* (2013.01); *A61K 2800/56* (2013.01)

(56) References Cited

U.S. PATENT DOCUMENTS

| | | | | |
|---|---|---|---|---|
| 10,328,024 | B2* | 6/2019 | Yoon | .................... A61K 31/352 |
| 2007/0253899 | A1 | 11/2007 | Ai et al. | |
| 2009/0069186 | A1 | 3/2009 | Shirley et al. | |
| 2010/0028257 | A1 | 2/2010 | Lazzari et al. | |
| 2017/0143628 | A1 | 5/2017 | Kim et al. | |
| 2017/0354576 | A1 | 12/2017 | Yoon et al. | |

OTHER PUBLICATIONS

Material Safety Data Sheet. Polymer Source, Mar. 14, 2008. <https://polymersource.com/browse2.php?ID=183>.

Nelson, C.E, "Balancing Cationic and Hydrophbic Content of PEGylated siRNA Polyplexes Enhances Endosome Escape, Stability, Blood, Circulation Time, and Bioactivity in Vivo." ACS Nano, Sep. 16, 2013, pp. 8870-8880.

Miteva, Martina, et al., "Tuning PEGylation of mixed micelles to overcome intracellular and systemic siRNA delivery barriers." Biomaterials, vol. 38, 2005, pp. 97-107.

Xing Yao-Hui et al: "Synthesis, self-assembly and responsive properties of PEG-b-PDMAEMA-b-PMMAzo triblock copolymers", Chinese Journal of Polymer Science. Zhongguo Huaxuehui. CN. vol. 31. No. 5. Apr. 20, 2013 (Apr. 20, 2013) pp. 833-840. XP035348585.

Yuhua Song et al: "Polycations with excellent gene transfection ability based on PVP-g-PDMAEMA with random coil and micelle structures as non-viral gene vectors", Journal of Materials Chemistry B. vol. 3. No. 5. Jan. 1, 2015 (Jan. 1, 2015) pp. 911-918. XP055460572.

Zhang X et al: "Synthesis of Well-Defined Amphiphilic Block Copolymers With 2-(Dimethylamino)Ethyl Methacrylate by Controlled Radical Polymerization". Macromolecules. American Chemical Society, vol. 32. No. 6. Mar. 23, 1999 (Mar. 23, 1999) pp. 1763-1766. XP000823803.

Seema Agarwal et al: "PDMAEMA based gene delivery materials", Materials Today,vol. 15. No. 9, Sep. 1, 2012 (Sep. 1, 2012). pp. 388-393. XP055460581.

Jiucun Chen et al: "Synthesis of linear amphiphilic tetrablock quaterpolymers with dual stimulus response through the combination of ATRP and RAFT by a click chemistry site transformation approach", Polymer Chemistry, vol. 1. No. 6. Jan. 1, 2013 (Jan. 1, 2013), p. 1815. XP055460643.

Extended European Search Report including Written Opinion for EP168610855 dated May 4, 2018.

* cited by examiner

AMPHIPHILIC POLYMER

CROSS-REFERENCE TO RELATED APPLICATION

The present application is a continuation of U.S. patent application Ser. No. 15/525,835, filed on May 10, 2017 which is a national phase entry under 35 U.S.C. § 371 of International Application No. PCT/KR2016/010623, filed Sep. 23, 2016 which claims priority to Korean Patent Application No. 10-2015-0165873, filed Nov. 25, 2015, the disclosures of which are incorporated herein by reference.

BACKGROUND

1. Field of the Invention

The present application relates to an amphiphilic polymer, a method of preparing the same, a micelle including the amphiphilic polymer and a composition thereof.

2. Discussion of Related Art

In the fields of pharmaceuticals and cosmetics, there has been a need to develop a formulation capable of stably loading various materials which are effective for skin into a product as well as enhancing the condition of the skin by effectively acting on the skin.

However, most drugs combine or react with other materials because of insolubility or instability, thus destabilizing the entire system.

Accordingly, various technologies for loading an effective drug more stably and easily into a formulation have been developed, and examples of the technologies include nanoemulsions prepared by forming emulsion particles into nanoscale particles, liposomes prepared by the self-assembly properties of phospholipids, solid lipid nanoparticles obtained by forming a solid lipid into nanoparticles, polymer nanoparticles with an interface stabilized by a surfactant, etc.

However, these nanoparticles also have many problems from the viewpoint of the insolubility problem of a target drug and the improvement of the percutaneous absorption effect according to dispersion properties.

RELATED ART DOCUMENT (Patent Document) JP Laid-open Patent Publication No. 2009-155282

SUMMARY OF THE INVENTION

The present application provides an amphiphilic polymer capable of effectively encapsulating a drug as well as having excellent dispersion properties, and a method of preparing the same.

Furthermore, the present application provides a micelle including an amphiphilic polymer which is effectively dispersed in water or oil and is capable of exhibiting excellent percutaneous absorption properties, and a composition including the micelle.

The present application relates to an amphiphilic polymer and a micelle. The micelle includes a drug encapsulated by an amphiphilic polymer.

The amphiphilic polymer according to the present application is a triblock copolymer which can exhibit phase separation properties, and effectively encapsulates a drug by self-assembly properties thereof, and can also be included in the pharmaceutical composition or cosmetic composition while having excellent dispersion properties.

In the present application, the term "amphiphilic polymer" may refer to a polymer having regions with different physical properties, for example, different solubility parameters, and an example thereof may be a polymer including both a hydrophobic region and a hydrophilic region.

In the present application, the term "hydrophilic or hydrophobic region" refers to a region, for example, which is included in a polymer while forming a block, in a state in which each region can be determined to be phase-separated, and the extent of hydrophilicity or hydrophobicity of each region is relative.

In the present application, the term "self-assembly properties" refers to a phenomenon in which an amphiphilic polymer spontaneously causes fine phase separation in a solution to have regularity and uniformity in size.

The amphiphilic polymer according to the present application includes a first block (A) and a second block (B) which is phase-separated from the first block (A). Moreover, the second block (B) includes a polymerization unit (B1) of an acrylic monomer or vinyl-based monomer of which a homopolymer has a solubility parameter of less than 10.0 $(cal/cm^3)^{1/2}$ and a polymerization unit (B2) of a polymerizable monomer having a functional group which is capable of forming a hydrogen bond.

The amphiphilic polymer according to the present application includes two blocks that are phase-separated from one another while having a polymerization unit of a polymerizable monomer having a functional group at a hydrophobic region, and thus has a remarkable drug loading capability to achieve stability of a micelle.

In the present application, the term "phase-separated from each other" denotes a state in which the first block and the second block are not mixed with each other, and form their own blocks when no external action is applied.

The amphiphilic polymer according to the present application includes the first block (A) and the second block (B) which is phase-separated from the first block (A).

The first block (A) refers to a hydrophilic region of the amphiphilic polymer, and for example, may include a polymer with a solubility parameter of 10 $(cal/cm^3)^{1/2}$ or more.

A calculation method of the solubility parameter is not particularly limited, and may follow methods known in the art. For example, the parameter may be calculated or obtained using a method known in the field as a Hansen solubility parameter (HSP).

In another embodiment, the first block (A) may include a polymer having a solubility parameter of 13 $(cal/cm^3)^{1/2}$ or more, 14 $(cal/cm^3)^{1/2}$ or more, 15 $(cal/cm^3)^{1/2}$ or more, 16 $(cal/cm^3)^{1/2}$ or more or 17 $(cal/cm^3)^{1/2}$ or more. The upper limit of the solubility parameter of the first block (A) is not particularly limited, and for example, may be 25 $(cal/cm^3)^{1/2}$ or less, or 23 $(cal/cm^3)^{1/2}$ or less.

The first block (A) may include any known polymer as long as the polymer satisfies the aforementioned solubility parameter and is capable of forming a hydrophobic region of the amphiphilic polymer which can load a drug according to the present application.

In an embodiment, the first block (A) may be one or more selected from the group consisting of a polyethylene glycol, a polyethylene glycol-propylene glycol copolymer, a polyvinylpyrrolidone and a polyethyleneimine.

Specifically, the first block (A) may be, but is not limited to, a polyethylene glycol having a number average molecular weight in the range of 500 to 100,000. In the present application, the term "number average molecular weight" may refer to an analysis numeric value measured by a nuclear magnetic resonator (NMR). Unless otherwise defined, the molecular weight of a polymer may denote the number average molecular weight of the polymer.

The second block (B) includes a polymerization unit (B1) of an acrylic monomer or vinyl-based monomer of which a homopolymer has a solubility parameter of less than 10.0 $(cal/cm^3)^{1/2}$ and a polymerization unit (B2) of a polymerizable monomer having a functional group which is capable of forming a hydrogen bond.

In the present application, the term "acrylic monomer" refers to (meth)acrylic acid or a derivative thereof. Furthermore, the term "(meth)acrylic acid" denotes acrylic acid or methacrylic acid.

As will be described below, the second block (B) of the amphiphilic polymer according to the present application is a portion that is adjacent to a drug to surround the drug and serves to form the overall shape of a micelle.

Consequently, the second block (B) denotes a relatively hydrophobic portion in the amphiphilic polymer, and includes a polymerization unit (B1) of an acrylic monomer or vinyl-based monomer of which a homopolymer has a solubility parameter of less than 10.0 $(cal/cm^3)^{1/2}$ and a polymerization unit (B2) of a polymerizable monomer having a functional group which is capable of forming a hydrogen bond.

In another embodiment, the second block (B) may include a polymerization unit (B1) of an acrylic monomer or vinyl-based monomer of which a homopolymer has a solubility parameter of less than 9.8 $(cal/cm^3)^{1/2}$ or less than 9.5 $(cal/cm^3)^{1/2}$. The lower limit of the solubility parameter of the acrylic monomer or vinyl-based monomer is not particularly limited, and for example, may be 2 $(cal/cm^3)^{1/2}$ or more, or 4 $(cal/cm^3)^{1/2}$ or more.

An example of the acrylic monomer may be a compound represented by the following Formula 1 or 2, but is not limited thereto.

[Formula 1]

[Formula 2]

In Formulas 1 and 2, Q is hydrogen or an alkyl group, in Formula 1, B is a linear or branched alkyl group with one or more carbon atoms, an alicyclic hydrocarbon group, an aromatic substituent or a carboxyl group, and in Formula 2, $R_1$ and $R_2$ each independently represent hydrogen, a linear or branched alkyl group with one or more carbon atoms, an alicyclic hydrocarbon group, or an aromatic substituent.

In Formulas 1 and 2, an alkyl group existing at Q may be an alkyl group having 1 to 20 carbon atoms, 1 to 16 carbon atoms, 1 to 12 carbon atoms, 1 to 8 carbon atoms or 1 to 4 carbon atoms. The alkyl group may be a linear, branched or cyclic alkyl group. Furthermore, the alkyl group may be optionally substituted with one or more substituents.

In Formulas 1 and 2, B, $R_1$ and $R_2$ may each independently represent a linear or branched alkyl group with 1 or more, 3 or more, 5 or more, 7 or more or 9 or more carbon atoms, and may be optionally substituted or unsubstituted. Such a compound having a relatively long-chain alkyl group is known as a hydrophobic compound. The upper limit of the number of carbon atoms of the linear or branched alkyl group is not particularly limited, and for example, the alkyl group may be an alkyl group with 20 or fewer carbon atoms.

In another embodiment, in Formulas 1 and 2, B, $R_1$ and $R_2$ may be an alicyclic hydrocarbon group, for example, an alicyclic hydrocarbon group with 3 to 20, 3 to 16 or 6 to 12 carbon atoms, and an example of the hydrocarbon group includes an alicyclic alkyl group with 3 to 20, 3 to 16 or 6 to 12 carbon atoms, such as a cyclohexyl group, an isobornyl group, etc. Such a compound having an alicyclic hydrocarbon group is also known as a relatively hydrophobic compound.

In another embodiment, in Formulas 1 and 2, B, $R_1$ and $R_2$ may be an aromatic substituent such as an aryl group, an aryl alkyl group, etc.

In the above description, the aryl group may be, for example, an aryl group with 6 to 24, 6 to 18 or 6 to 12 carbon atoms. Further, the alkyl group of the aryl alkyl group may be, for example, an alkyl group with 1 to 20, 1 to 16, 1 to 12, 1 to 8 or 1 to 4 carbon atoms. An example of the aryl group or the aryl alkyl group includes a phenyl group, a phenylethyl group, a phenylpropyl group, a naphthyl group or the like, but is not limited thereto.

In the present application, examples of the substituent which may optionally substitute an alkyl group, an aryl group, a hydrocarbon group or the like in Formulas 1 and 2 include a halogen such as chlorine or fluorine, a glycidyl group, an epoxy group such as an epoxy alkyl group, a glycidoxy alkyl group or an alicyclic epoxy group, an acryloyl group, a methacryloyl group, an isocyanate group, a thiol group, an alkyl group, an alkenyl group, an alkynyl group, an aryl group or the like, but are not limited thereto.

The compound represented by Formula 1 may be, for example, an alkyl (meth)acrylate. In the above description, the term "(meth)acrylate" refers to acrylate or methacrylate. Examples of the alkyl (meth)acrylate include methyl (meth)acrylate, ethyl (meth)acrylate, n-propyl (meth)acrylate, isopropyl (meth)acrylate, n-butyl (meth)acrylate, t-butyl (meth)acrylate, sec-butyl (meth)acrylate, pentyl (meth)acrylate, hexyl (meth)acrylate, 2-ethylhexyl (meth)acrylate, 2-ethylbutyl (meth)acrylate, n-octyl (meth)acrylate, isobornyl (meth)acrylate, isooctyl (meth)acrylate, isononyl (meth)acrylate, lauryl (meth)acrylate or the like, but are not limited thereto.

In the present application, a suitable monomer among the monomers described above may be used in consideration of the desired physical properties of the amphiphilic polymer.

In an embodiment, in Formula 1, Q may be hydrogen or an alkyl group with 1 to 4 carbon atoms, and B may be an alkyl group with 7 or more carbon atoms or an alicyclic hydrocarbon group with 6 to 12 carbon atoms, but they are not limited thereto.

The second block (B) may include a polymerization unit (B1) of a vinyl-based monomer of which a homopolymer has a solubility parameter of less than 10 $(cal/cm^3)^{1/2}$.

For example, the vinyl-based monomer may be a compound represented by the following Formula 3 or 4.

[Formula 3]

In Formula 3, X is a nitrogen atom or an oxygen atom, Y is a carbonyl group or a single bond, $R_3$ and $R_5$ each independently represent hydrogen or an alkyl group, $R_3$ and $R_5$ are connected to each other to form an alkylene group, and $R_4$ is an alkenyl group (but, when X is an oxygen atom, $R_3$ is not present);

[Formula 4]

In Formula 4, $R_6$, $R_7$ and $R_8$ each independently represent hydrogen or an alkyl group, and $R_9$ is a cyano group or an aromatic substituent.

In Formula 3, when Y is a single bond, a structure in which there is no separate atom at the part represented as Y, and $R_5$ and X are directly connected may be realized.

In Formula 3, $R_4$ may be, for example, a linear, branched or cyclic alkenyl group with 2 to 20, 2 to 16, 2 to 12, 2 to 8 or 2 to 4 carbon atoms, and may be optionally substituted or unsubstituted. Generally, a vinyl group, an allyl group or the like may be used as the alkenyl group.

In Formula 3, $R_3$ and $R_5$ may each independently represent hydrogen or a linear, branched or cyclic alkyl group with 1 to 20, 1 to 16, 1 to 12, 1 to 8 or 1 to 4 carbon atoms, or may be connected to one another to form an alkylene group with 1 to 20, 2 to 16, 2 to 12 or 2 to 8 carbon atoms. In the above description, when $R_3$ and $R_5$ form an alkylene group, the compound of Formula 3 may be a cyclic compound.

Examples of the vinyl-based monomer represented by Formula 3 or 4 include a styrene-based monomer such as styrene or methyl styrene; acrylonitrile; an amide-based monomer such as an N-vinyl amide compound; an ester-based monomer such as a vinyl ester compound; or an ether-based monomer such as a vinyl ether compound or the like, but are not limited thereto, and any vinyl-based monomer may be used as the vinyl-based monomer included as a polymerization unit in the amphiphilic polymer according to the present application without limitation as long as the vinyl-based monomer satisfies the aforementioned solubility parameter of the homopolymer.

Furthermore, the second block (B) includes a polymerization unit (B2) of a polymerizable monomer having a functional group which is capable of forming a hydrogen bond.

The amphiphilic polymer according to the present application has the second block (B) including both the polymerization unit (B1) of an acrylic monomer or vinyl-based monomer and the polymerization unit (B2) of a polymerizable monomer having a functional group which is capable of forming a hydrogen bond, such that the capability of loading a target drug can be enhanced and a drug can be more suitably positioned at the core of a micelle.

In the above description, the polymerizable monomer having a functional group which is capable of forming a hydrogen bond may denote a polymerizable monomer other than the aforementioned acrylic monomer and vinyl-based monomer, having a functional group which is capable of forming a hydrogen bond.

In an embodiment, the functional group which is capable of forming a hydrogen bond of the polymerizable monomer may be, but is not limited to, a hydroxyl group, an amine group, a nitro group, an amino group, an imide group, an alkoxysilane group, a cyano group or the like, and is not particularly limited as long as the functional group serves as an electron donor which can increase the capability of loading a drug and have a drug stably positioned at the core of a micelle by interacting with —H, specifically, forming a hydrogen bond with —H in a drug, that will be described below.

Examples of the polymerizable monomer having an amine group include 2-aminoethyl (meth)acrylate, 3-aminopropyl (meth)acrylate, N,N-dimethylaminoethyl (meth)acrylate, N,N-dimethylaminopropyl (meth)acrylate or the like, but are not limited thereto.

Examples of the polymerizable monomer having an alkoxysilane group include vinyl alkoxysilanes, allyl alkoxysilanes, (meth)acryloxyalkyl alkoxysilanes, vinyl acryloxy silanes, etc. Further, examples of the (meth)acryloxyalkyl alkoxysilanes include, 3-(meth)acryloxypropyl methyldimethoxy silane, 3-(meth)acryloxypropyl methyldiethoxysilane, 3-(meth)acryloxypropyl trimethoxysilane, 3-(meth)acryloxypropyl triethoxysilane, (meth)acryloxymethyl triethoxysilane or (meth)acryloxymethyl tris(trimethylsiloxy) silane or the like, but are not limited thereto.

Examples of the polymerizable monomer having a cyano group include cyanomethyl (meth)acrylate, cyanoethyl (meth)acrylate, or cyanopropyl (meth)acrylate, but are not limited thereto.

Such a polymerizable monomer capable of forming a hydrogen bond forms the polymerization unit (B2) in the second block (B), and for example, the polymerization unit (B2) may be positioned at an outer side of the polymer to act to load a drug.

Furthermore, the second block (B) may include the polymerization unit (B1) of an acrylic monomer or vinyl-based monomer and the polymerization unit (B2) capable of forming a hydrogen bond of the polymerizable monomer in a predetermined weight ratio.

For example, the weight ratio (B1:B2) of the polymerization unit (B1) of an acrylic monomer or vinyl-based monomer of which a homopolymer has a solubility parameter of less than 10.0 $(cal/cm^3)^{1/2}$ to the polymerization unit (B2) which has a polymerizable group capable of forming a hydrogen bond may be the same or different. For example, the weight ratio (B1:B2) may be in the range of 1:9 to 9:1. In another embodiment, the weight ratio (B1:B2) may be in the range of 2:8 to 8:2, 3:7 to 7:3 or 4:6 to 6:4. When the weight ratio (B1:B2) is within this range, an amphiphilic polymer can effectively load a drug and be stably dispersed in an aqueous solution.

For example, the second block (B) may have a number average molecular weight in the range of 500 to 100,000. Within this range, the desired hydrophobic property and capability of loading a drug can be secured.

Moreover, the block ratio (A:B) of the first block (A) and the second block (B) of the amphiphilic polymer according to the present application may be the same or different.

In an embodiment, the block ratio (A:B) of the first block (A) and the second block (B) of the amphiphilic polymer according to the present application may be different.

Specifically, the amphiphilic polymer according to the present application may have the block ratio (A:B) of the first block (A) to the second block (B) controlled to 1:9 to 9:1. In the above description, the term "block ratio (A:B)" refers to a weight ratio between the blocks.

In another embodiment, the block ratio (A:B) of the first block (A) to the second block (B) may be 2:8 to 8:2, 3:7 to 7:3, or 4:6 to 6:4.

The amphiphilic polymer may have a number average molecular weight (Mn) in the range of 1,000 to 1,000,000.

Furthermore, the present application relates to a micelle including the aforementioned amphiphilic polymer.

In the present application, the term "micelle" may refer to a particle ranging in size from several nanometers to tens of thousands of nanometers in diameter and having a core-shell structure due to self-assembly properties of an amphiphilic polymer.

The micelle including the amphiphilic polymer according to the present application may have excellent dispersion properties in water or oil as well as high stability.

For example, the micelle may further include a drug encapsulated by an amphiphilic polymer.

Figure 1:
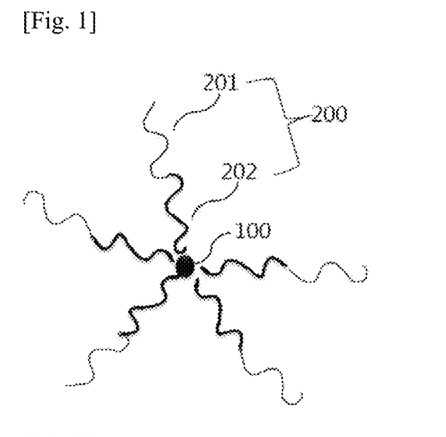
FIG. 1 is a schematic view of a micelle including the amphiphilic polymer according to the present application.

In an embodiment, as shown in FIG. 1, the micelle according to the present application may have a structure with a drug and an amphiphilic polymer encapsulating the drug. Furthermore, the amphiphilic polymer includes a first block and second block, and any one of the second blocks of the amphiphilic polymer may have a structure adjacent to a drug. In the above description, the term "encapsulation" refers to a structure in which an amphiphilic polymer surrounds a drug, and has the same meaning as "loading" in the present application.

While drugs are generally insoluble, the drug according to the present application is encapsulated by the amphiphilic polymer having both a hydrophobic region and a hydrophilic region, thus securing excellent dispersion properties of a drug in water or oil.

Furthermore, in the present application, a drug is encapsulated by the amphiphilic polymer with the second block (B) having the polymerization unit (B2) which has a polymerizable group capable of forming a hydrogen bond, and thus a micelle having an excellent drug loading capability and securing stability can be provided.

Moreover, the micelle according to the present application has a structure with a drug encapsulated by the amphiphilic polymer which has the same or different block ratio (A:B) of the first block (A) to the second block (B), and thus can secure the superiority of the aforementioned dispersion properties.

For example, the drug included in the micelle of the present application may include a biologically active substance, but is not particularly limited.

In an embodiment, the biologically active substance may be insoluble.

The biologically active substance may be, for example, one or more selected from the group consisting of genistein, daidzein, cucurbitacin, prangenidin or a derivative thereof; a polyphenol; or a mixture thereof.

As an example of the biologically active substance, the genistein, daidzein, cucurbitacin, prangenidin or the derivative thereof refers to a phenolic compound or a glycoside thereof contained in the soybean, that has a structure similar to estrogen which is a female hormone, exhibits an excellent antioxidative effect or the like, and is being used in a wide range of applications such as skin care, anticancer therapy, etc.

Specifically, the isoflavone may be genistein or a glycoside of the genistein, for example, acetyl genistein, malonyl genistein or the like, but is not limited thereto. An isoflavone such as the genistein, daidzein, cucurbitacin, prangenidin or the derivative thereof is a phenolic compound, which includes —H in its molecule, and the —H in its molecule forms a hydrogen bond with the functional group capable of forming a hydrogen bond in the second block (B) of the amphiphilic polymer to improve stability of a drug positioned inside of a micelle.

The drug contained in the micelle may be included in the micelle at an amount by which the micelle can exhibit physiological activity when prepared as a formulation.

In an embodiment, the content of the drug may be in the range of 1 to 60 wt %, 1 to 50 wt %, 1 to 40 wt % or 1 to 20 wt % based on the total weight of the micelle. When the content of the drug exceeds 60 wt %, effective loading cannot be performed, and the drug leaks out of the micelle and agglomerates in a crystalline form or is denatured.

Such a micelle may have, for example, an average particle size in the range of 1 to 10,000 nm. The average particle size of the micelle is a value measured using a dynamic light scattering method, and may be within the range including the particle size of a single micelle or micelle aggregates.

Furthermore, the present application relates to a composition including the aforementioned micelle.

In an embodiment, the present application relates to a composition for preparing a particle, which includes the micelle containing the amphiphilic polymer.

The composition for preparing a particle according to the present application includes a micelle formed due to self-assembly properties of the amphiphilic polymer. Moreover, the amphiphilic polymer forming this micelle, for example, may encapsulate a drug.

For example, the micelle included in the composition for preparing a particle may further contain a drug encapsulated by an amphiphilic polymer.

Furthermore, the present application relates to a pharmaceutical or cosmetic composition, including the micelle which contains the amphiphilic polymer.

Specifically, the micelle included in the pharmaceutical or cosmetic composition may contain an amphiphilic polymer and a drug encapsulated by the amphiphilic polymer.

In an embodiment, when the composition is a pharmaceutical composition, the drug in the micelle may be included in the composition in a pharmaceutically acceptable form. Further, the pharmaceutical composition may additionally include a pharmaceutically acceptable carrier.

Moreover, the pharmaceutical composition may be formulated for oral or non-oral administration.

In formulating the pharmaceutical composition, commonly used excipients or diluents such as fillers, bulking agents, binders, wetting agents, disintegrating agents, and surfactants may be used.

In an embodiment, solid formulations for oral administration include tablet, bolus, powder, granule, capsule and the like, and the solid formulation may be prepared by mixing one or more of the active components with at least one excipient such as starch, calcium carbonate, sucrose, lactose, gelatin, etc.

In an embodiment, liquid formulations for oral administration are suspensions, solutions, emulsions and syrups, and the aforementioned formulations may contain various excipients such as wetting agents, sweeteners, aromatics, preservatives or the like in addition to generally used simple diluents such as water and liquid paraffin. Examples of formulations for parenteral administration include sterilized aqueous solutions, water-insoluble excipients, suspensions, emulsions, lyophilized preparations and suppositories.

The pharmaceutical composition may be formulated in any type suitable for pharmaceutical preparations, including oral preparations such as powder, granule, tablet, capsule, suspension, emulsion, syrup, aerosol or the like, external preparations such as ointment, cream or the like, suppository or sterilized solution for injection, etc. using a common method.

In another embodiment, the composition may be, for example, a cosmetic composition that may be contained in an external preparation for the skin, having formulations such as skin lotion, skin softener, skin toner, astringent, nutrition toner, nutrition cream, cleansing foam, essence, pack, etc.

The cosmetic composition and external preparation for the skin may further include known additive components, for example, including a powder base or carrier such as a binder, a disintegrant, an excipient, a lubricant or the like, an oily base or carrier such as animal and vegetable oils, waxes, vaseline, paraffin oil, silicone oil, a higher fatty acid ester, a higher fatty acid or the like, an aqueous base or carrier such as a gel base including a xanthan gum or the like, preservatives, chelating agents, antioxidants, refreshing agents, stabilizers, fluidizing agents, shear-thickening agents, buffering agents, dispersing agents, absorbents, moisturizing agents, wetting agents, desiccants, antistatic agents or other resins such as a polyamide-based resin, an olefin-based resin such as a hydrogenated polybutene, etc.

The pharmaceutical composition or cosmetic composition may be in the form of a water-in-oil or oil-in-water emulsion.

For example, the micelle in the composition may form aggregates. The micelle aggregates may be formed due to a van der Waals' force between the hydrophobic regions. For example, the micelle aggregates may have a size in the range of 10 to 10,000 nm.

Further, the present application relates to a method of preparing the aforementioned amphiphilic polymer.

That is, the preparation method according to the present application includes polymerizing a polymer which forms a first block (A) with an acrylic monomer or vinyl-based monomer of which a homopolymer has a solubility parameter of less than 10.0 $(cal/cm^3)^{1/2}$.

Specifically, in the method of preparing the amphiphilic polymer according to the present application, an example of a method of polymerizing the polymer which forms a first block (A) with the aforementioned monomer may be a living radical polymerization method, for example, an atom transfer radical polymerization (ATRP) method to effectively achieve narrow molecular weight distribution and a desired molecular weight, but is not particularly limited thereto.

More specifically, the amphiphilic polymer according to the present application may be prepared by reacting the polymer which forms the first block (A) and includes a halogen atom with a transition metal complex catalyst to generate radicals for receiving electrons at a double bond site of an acrylic monomer or vinyl-based monomer for forming the second block, and forming second block (B) with a polymerization unit (B1) of an acrylic monomer or vinyl-based monomer and a polymerization unit (B2) having a functional group which is capable of forming a hydrogen bond, but is not limited thereto.

For example, the polymer which forms the first block is a polymer that does or does not include a halogen atom, and has a solubility parameter of 10 $(cal/cm^3)^{1/2}$ or more. When a polymer for forming the first block that does not include a halogen atom is used, a step of preparing an initiator for ATRP by the reaction with a compound including a halogen atom may be further included.

Furthermore, the present application relates to a method of preparing a micelle, which includes mixing a drug with the amphiphilic polymer prepared as above.

A method for mixing an amphiphilic polymer and a drug to prepare the micelle is not particularly limited, and for example, the method may include dissolving a predetermined organic solvent such as ethanol or the like with the amphiphilic polymer and mixing the solution thus prepared with a solution containing a drug.

Furthermore, a process of removing the solvent may be included as a subsequent process after the aforementioned process, but the present application is not limited thereto, and the method may additionally involve a known process between each of the processes or as a subsequent process.

A temperature in the process of removing the solvent is different according to the boiling point of each solvent, and for example, the solvent may be removed at a temperature of 50° C. or more, but the present application is not limited thereto.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, the present application will be described in detail with reference to examples, but the following examples are only examples within the gist of the present application. Meanwhile, it is apparent to those skilled in the art that the present application is not limited to process conditions proposed by the following examples but may be arbitrarily selected within a range required to achieve the objects of the present application.

Example 1. Preparation of Amphiphilic Polymer P1

After a polyethyleneglycol monomethyl ether polymer (molecular weight: 5000, purchased from Sigma-Aldrich Co. Llc) forming a first block was dissolved in dichloromethane at a concentration of 30%, 3 equivalent weights of triethylamine and 2 equivalent weights of 2-bromo isobutyryl bromide were introduced with respect to a —OH group to perform a reaction, thereby preparing an initiator for ATRP. Then, a process of precipitation and loading of the initiator in a diethyl ether solvent was repeated twice and drying was performed to remove impurities and obtain a polyethylene glycol polymer at bromine end groups. 100 parts by weight of the polyethylene glycol polymer with bromine end groups thus obtained was dissolved in 250 parts by weight of an anisole-containing reaction solvent in a flask, methyl methacrylate with a solubility parameter of 9.5 $(cal/cm^3)^{1/2}$) and N,N-dimethylaminoethyl methacrylate with a solubility parameter of 9.6 $(cal/cm^3)^{1/2}$ were added thereto in the weight ratio of 80:20, and a flask was sealed with a rubber stopper. Thereafter, nitrogen purging and stirring were carried out at room temperature for 30 minutes to remove dissolved oxygen, the flask was dipped in an oil bath with a temperature set to 60° C., and a copper (II) bromide complex and a catalytic reducing agent were introduced thereinto to perform a reaction. When a desired molecular weight was obtained, the reaction was completed, thereby preparing an amphiphilic polymer P1 with a B-A-B triblock structure. The molecular weight and the ratio B:A:B of each block of the triblock of the amphiphilic polymer P1 are shown below in Table 1.

Example 2. Preparation of Amphiphilic Polymer P2

An amphiphilic polymer P2 with a triblock structure (B-A-B) was prepared in the same manner as in Example 1 except that methyl methacrylate with a solubility parameter of 9.5 $(cal/cm^3)^{1/2}$ and N,N-dimethylaminoethyl methacrylate with a solubility parameter of 9.6 $(cal/cm^3)^{1/2}$ were added thereto in the weight ratio of 60:40. The molecular weight, the ratio B:A:B of each block of the triblock and the weight ratio B1:B2 of polymerization units in the second block (B) of the amphiphilic polymer P2 are shown below in Table 1.

Comparative Example 1

A polycaprolactone (B)-polyethylene glycol (A)-polycaprolactone (B) copolymer P4, in which a polycaprolactone with a solubility parameter of approximately 10 $(cal/cm^3)^{1/2}$ which is a polyester-based polymer was used, was prepared by the following method.

Specifically, the synthesis was conducted through ring-opening polymerization with a polyethylene glycol polymer (molecular weight: 2000, purchased from Daejung Chemical & Metal Co.) as an initiator. Stannous 2-ethyl-hexanoate $(Sn(Oct)_2)$ was used as a catalyst. The polyethylene glycol and $Sn(Oct)_2$ were dried at 110° C. under vacuum conditions for 4 hours in a 2-neck round flask to eliminate moisture, and a reactor was cooled to room temperature. ε-Caprolactone was added in the same amount as polyethyleneglycol monoethyl ether in the reactor in a nitrogen atmosphere and vacuum-dried at 60° C. for 1 hour. The reactor was gradually cooled to 130° C. in a nitrogen atmosphere to perform a reaction for 18 hours, and cooled to room temperature again to complete the reaction. Methylene chloride was added to the reactor cooled to room temperature to dissolve a reactant, and an excess amount of cold ethyl ether was gradually added to precipitate a copolymer. The precipitated block copolymer was filtered and vacuum-dried at 40° C. for 48 hours to finally obtain a polycaprolactone (B)-polyethylene glycol (A)-polycaprolactone (B) copolymer P4.

Comparative Example 2. Preparation of Amphiphilic Polymer P4

The amphiphilic polymer P4 was prepared in the same manner as in Comparative Example 1 except that the amount of added ε-caprolactone was twice the amount of polyethyleneglycol monoethyl ether during the synthesis of a polyethylene glycol (A)-polycaprolactone (B) copolymer in which a polycaprolactone with a solubility parameter of approximately 10 $(cal/cm^3)^{1/2}$ which is a polyester-based polymer was used.

Experimental Example 1. Evaluation of Block Ratio B:A:B of Prepared Amphiphilic Polymer The block ratio of the prepared amphiphilic polymers P1 to P5 was evaluated by the following method and the results are shown in Table 1.

Specifically, the polymer solution from which the catalyst was completely removed underwent a purification process to be solidified, and the block ratio of the amphiphilic polymer was determined by 1H NMR analysis. The purification of the polymer solution was carried out by having the polymer solution pass through an alumina column to eliminate a copper complex catalyst, and adding the polymer solution dropwise into an excess amount of diethyl ether with stirring to remove the remaining monomer to be solidified. The solidified polymer was dried in a vacuum oven for 24 hours. The amphiphilic polymer purified by the aforementioned method was dissolved in a $CDCl_3$ solvent and measured using 1H-NMR analysis equipment. In the case of Examples 1 and 2 and Comparative Examples 1 and 2, as the analysis result, a 1H peak derived from $CH_2=C(CH_3)-$ at double-bond end groups was not determined, from which it can be seen that no unreacted monomer existed. Moreover, 3H peaks derived from $-OCH_3$ of ethylene glycol block end groups were confirmed at around 3.2 ppm, and thus the ratio and molecular weight of each copolymer block was calculated based on this. Approximately 450 of H peaks (4H×113 repeat units) derived from $-CH_2CH_2O-$ of ethylene glycol formed of the polymer were shown in a 3.6 to 3.8 ppm region, and in the case of Examples 1 and 2, 3H peaks derived from $-CH_3$ adjacent to a main chain of methyl methacrylate formed of the polymer were shown in a 3.5 to 3.6 ppm region, 2H peaks derived from $-OCH_2-$ adjacent to $-COO-$ of a side chain of dimethylaminoethyl methacrylate formed of the polymer were shown in a 4.0 to 4.2 ppm region, and thus the content of each constituent monomer was calculated as a mass fraction through the area ratio thereof. In the case of Comparative Examples 1 and 2, 2H peaks derived from the first $-CH_2-$ from the right of $-CO-$ in $-(CO-CH_2CH_2CH_2CH_2CH_2-O-)_n$ which is a chain of caprolactone formed of the polymer were shown in a 2.3 to 2.4 ppm region, and thus the molecular weight was confirmed by the area of 3H peaks derived from $-OCH_3$ of ethylene glycol block end groups and the area of 2H peaks derived from the first $-CH_2-$ from the right of $-CO-$ of caprolactone.

TABLE 1

|  | Molecular weight (Mn, second block:first block:second block) | Block ratio (B:A:B) | Weight ratio (B1:B2) of polymerization units of second block (B) (B1:B2)[a] |
|---|---|---|---|
| Example 1 | 11,000 (6,000:5,000:6,000) | 4.55:5.45:4.55 | 80:20 |
| Example 2 | 11,000 (6,000:5,000:6,000) | 4.55:5.45:4.55 | 60:40 |
| Comparative Example 1 | 9,900 (4,900:5,000:4,900) | 5.05:4.95:5.05 | — |

TABLE 1-continued

| | Molecular weight (Mn, second block:first block:second block) | Block ratio (B:A:B) | Weight ratio (B1:B2) of polymerization units of second block (B) (B1:B2)[a] |
|---|---|---|---|
| Comparative Example 2 | 14,700(9,700:5,000:9,700) | 0.34:0.66:0.34 | — |

[a]Mass ratio of methyl methacrylate (B1):N,N-dimethylaminoethyl methacrylate (B2)

Figure 2:
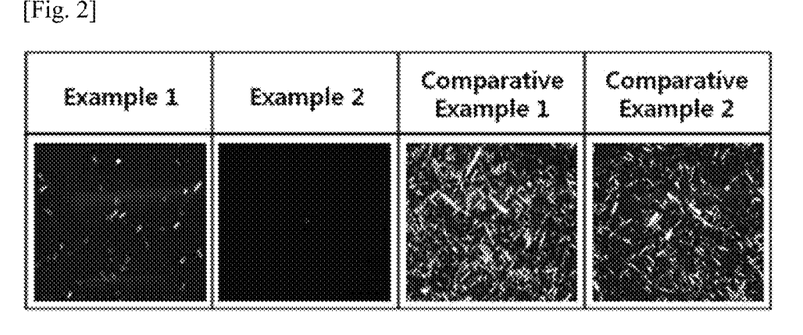
FIG. 2 shows images for determining precipitation of amphiphilic polymers according to examples and comparative examples and drugs encapsulated by the amphiphilic polymers.
Figure 3:
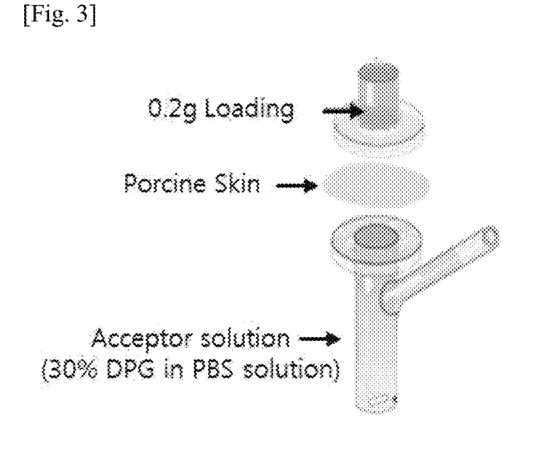
FIG. 3 is a schematic view of a Franz cell for a percutaneous absorption test.

Experimental Example 2. Preparation of Micelle and Determination of Dissolved Concentration of Drug Genistein which is an insoluble substance was loaded using the synthesized amphiphilic polymers P1 to P5. First, a solution obtained by dissolving 10 g of the amphiphilic polymer in 30 mL of ethanol was mixed with a solution obtained by dissolving 20 g of dipropylene glycol (DPG) in 2 g of genistein. After the mixed solution was introduced into 100 mL of a 0.5% polyvinyl alcohol aqueous solution with stirring, the remaining ethanol was eliminated using a rotary evaporator to prepare a solution in which the content of genistein was 2%. The prepared solution was diluted with 10 times as much distilled water and stored at room temperature (25° C.) for 7 days to determine whether property changes of the solution occurred over time using an optical microscope, and the results are shown in FIG. 2. Furthermore, after the solution was filtered using a syringe filter with a pore size of 1 μm to eliminate the precipitated genistein, the content of genistein loaded in an amphiphilic polymer micelle particle was measured by liquid chromatography (HPLC). The drug loading capacity and drug loading efficiency of the amphiphilic polymer were calculated according to the following equations, and the particle size of the amphiphilic polymer micelle in which a drug was loaded was measured using Zetasizer 3000 manufactured by Malvern Instruments, Inc.

$$\text{Drug loading capacity} = \frac{\text{Amount of impregnated drug}}{\text{Amount of impregnated drug} + \text{Content of block copolymer}} s100(\%) \quad [\text{Equation 1}]$$

$$\text{Drug loading efficiency} = \frac{\text{Amount of impregnated drug}}{\text{Initial drug dose}} s100(\%) \quad [\text{Equation 2}]$$

The results of measuring the particle size of the micelle and the resulting drug loading capacity and drug loading efficiency of the micelle are shown in the following Table 2.

TABLE 2

| | Example 1 | Example 2 | Comparative Example 1 | Comparative Example 2 |
|---|---|---|---|---|
| Particle size (nm) | 125 | 135 | 100 | 150 |
| Drug loading capacity (%) | 10.7 | 16.1 | 1.2 | 1.8 |
| Drug loading efficiency (%) | 60 | 96 | 6 | 9 |

Experimental Example 3. Percutaneous Absorption Test

The percutaneous absorption of genistein of the amphiphilic polymer solution in which genistein was loaded and which was prepared as above was evaluated using porcine skin (2×2 cm, thickness: 1000 μm) and a Franz diffusion cell. A phosphate buffered saline (PBS) solution containing 30 wt % of dipropylene glycol (DPG) was used as an aqueous solution (acceptor solution) to maintain a sink condition with respect to genistein. 0.2 g of the amphiphilic polymer solution on which genistein was loaded was loaded in a Franz diffusion cell on which the porcine skin was mounted, and the test was performed at 32° C. similar to a skin temperature for 24 hours. Skin tissue into which genistein was absorbed was pulverized and extracted to analyze the content of genistein absorbed into the skin tissue and the content of genistein absorbed into the acceptor solution through HPLC, and the results are shown in Table 3.

TABLE 3

| | Example 1 | Example 2 | Comparative Example 1 | Comparative Example 2 |
|---|---|---|---|---|
| Skin penetration amount (μg/cm$^2$) | 1.85 | 3.70 | 0.22 | 0.35 |
| Skin penetration ratio (%) | 1.05 | 2.10 | 0.13 | 0.20 |

The present application can provide an amphiphilic polymer that can effectively encapsulate a drug and have excellent dispersion properties in an aqueous solution, and a method of preparing the same.

Furthermore, the present application can provide a micelle that is effectively dispersed in water or oil, and capable of exhibiting excellent percutaneous absorption properties when prepared as a formulation, and a composition including the same.

The above description of the present invention is merely an example, and it will be apparent to those skilled in the art that various modifications can be made to the above-described exemplary embodiments of the present invention without departing from the spirit or scope of the invention. Thus, the above-described embodiments of the present invention are intended merely to be examples in all aspects and the present invention is not limited thereto.

What is claimed is:

1. A micelle comprising:
an amphiphilic polymer, comprising:
a first block (A); and
a second block (B) which is phase-separated from the first block (A) and includes a polymerization unit (B1) of an acrylic monomer or vinyl-based monomer of which a homopolymer has a solubility parameter of less than 10.0 (cal/cm$^3$)$^{1/2}$ and a polymerization unit (B2) of a polymerizable monomer having a functional group which is capable of forming a hydrogen bond,
wherein a weight ratio (B1:B2) of the polymerization unit (B1) of an acrylic monomer or vinyl-based monomer of which a homopolymer has a solubility parameter of less than 10.0 $(cal/cm^3)^{1/2}$ to the polymerization unit (B2) of a polymerizable monomer having a functional group which is capable of forming a hydrogen bond in the second block (B) is in a range of 1:9 to 9:1, and
a drug encapsulated by the amphiphilic polymer, wherein the second block (B) of the amphiphilic polymer is adjacent to the drug,
wherein the drug includes an insoluble biologically active substance,
wherein the insoluble biologically active substance is one or more selected from the group consisting of genistein, daidzein, cucurbitacin, prangenidin and a derivative thereof,
wherein the vinyl-based monomer is a compound represented by the following Formula 3 or 4:

[Formula 3]

where, in Formula 3, X is a nitrogen atom or an oxygen atom, Y is a carbonyl group or a single bond, $R_3$ and $R_5$ each independently represent hydrogen or an alkyl group, or $R_3$ and $R_5$ are connected to each other to form an alkylene group, and $R_4$ is an alkenyl group, provided that when X is an oxygen atom, $R_3$ is not present;

[Formula 4]

where, in Formula 4, $R_6$, $R_7$ and $R_8$ each independently represent hydrogen or an alkyl group, and $R_9$ is a cyano group or an aromatic substituent.

2. The micelle of claim 1, wherein the first block (A) includes a polymer having a solubility parameter of 10.0 $(cal/cm^3)^{1/2}$ or more.

3. The micelle of claim 1, wherein the first block (A) includes at least one polymer selected from the group consisting of a polyethylene glycol, a polyethylene glycol-propylene glycol copolymer, a polyvinylpyrrolidone and a polyethyleneimine.

4. The micelle of claim 1, wherein the acrylic monomer is a compound represented by the following Formula 1 or 2:

[Formula 1]

[Formula 2]

where, in Formulas 1 and 2, Q is hydrogen or an alkyl group,
in Formula 1, B is a linear or branched alkyl group with one or more carbon atoms, an alicyclic hydrocarbon group, an aromatic substituent or a carboxyl group, and
in Formula 2, $R_1$ and $R_2$ each independently represent hydrogen, a linear or branched alkyl group with one or more carbon atoms, an alicyclic hydrocarbon group, or an aromatic substituent.

5. The micelle of claim 4, wherein, in Formula 1, Q is hydrogen or an alkyl group with 1 to 4 carbon atoms, and B is an alkyl group with one or more carbon atoms or an alicyclic hydrocarbon group with 6 to 12 carbon atoms.

6. The micelle of claim 1, wherein the functional group is a hydroxyl group, an amine group, a nitro group, an amino group, an imide group, an alkoxysilane group or a cyano group.

7. The micelle of claim 1, wherein a block ratio (A:B) of the first block (A) and the second block (B) is different.

8. The micelle of claim 1, wherein a block ratio (A:B) of the first block (A) to the second block (B) is in a range of 1:9 to 9:1.

9. The micelle of claim 1, wherein a block ratio (A:B) of the first block (A) to the second block (B) is in a range of 3:7 to 7:3.

10. The micelle of claim 1, wherein an average particle size is in a range of 1 to 10,000 nm.

11. A composition for preparing a particle, comprising the micelle of claim 1.

12. A pharmaceutical or cosmetic composition, comprising the micelle of claim 1.

13. The pharmaceutical or cosmetic composition of claim 12, which is in the form of water-in-oil or oil-in-water emulsion.

* * * * *